United States Patent [19]
Fredrickson

[11] Patent Number: 4,814,433
[45] Date of Patent: Mar. 21, 1989

[54] METHOD FOR OBTAINING A PAPAIN-FREE ANTIBODY FRAGMENT PREPARATION

[75] Inventor: Robert A. Fredrickson, Elkhart, Ind.

[73] Assignee: Miles Inc., Elkhart, Ind.

[21] Appl. No.: 97,115

[22] Filed: Sep. 16, 1987

[51] Int. Cl.[4] ............................................. A61K 39/395
[52] U.S. Cl. ...................................... 530/388; 435/68; 435/69; 530/387; 424/85
[58] Field of Search ................... 530/387, 388; 435/68, 435/69; 424/85

[56] References Cited

U.S. PATENT DOCUMENTS

| | | | |
|---|---|---|---|
| 4,479,934 | 10/1984 | Sedlarek et al. | 424/85 |
| 4,719,107 | 1/1988 | Carosella et al. | 424/85 |
| 4,742,159 | 5/1988 | Batz et al. | 530/388 |

OTHER PUBLICATIONS

Biochem. J., 73:(1959), 119-126, Porter.
J. Immunol. Methods, 53 (1982), 133-173, Parham et al.

*Primary Examiner*—Howard E. Schain
*Attorney, Agent, or Firm*—Daniel W. Collins

[57] ABSTRACT

A method for obtaining a papain-free $F(ab')_2$ antibody fragment preparation derived from papain digested whole IgG antibody employing an antibody to papain for binding to and removing papain-associated digestion products from the preparation. The method is particularly useful for digesting whole IgG antibodies which are otherwise sensitive to pepsin digestion to provide $F(ab')_2$ antibody fragments from which $Fab'$ antibody fragments can be obtained having available free sulfhydryl groups in the hinge region.

11 Claims, No Drawings

METHOD FOR OBTAINING A PAPAIN-FREE ANTIBODY FRAGMENT PREPARATION

BACKGROUND OF THE INVENTION

The present invention relates to the proteolytic digestion of whole antibodies to obtain antibody fragments therefrom. In particular, the present invention relates to the preparation of F(ab')$_2$ antibody fragments derived from papain digested whole IgG antibodies.

The use of monovalent [Fab and Fab'] and divalent [F(ab')$_2$] antibody fragments derived from whole IgG antibodies is well established. For example, such fragments have been employed as labeled immunoassay reagents [Ullman, et al, *Methods in Enzymology*, Vol. 74, p 28 (1981); Inoue, et al., *Analytical Letters*, vol. 18, p. 1331 (1985); and German Patent Application No. DE 3430905] and as immunotherapeutic agents [Smith, et al., *Antibodies in Human Diagnosis and Therapy*, Haber and Krause (Eds.), Raven Press, New York, N.Y., p. 365 (1977)]. In the area of immunodiagnostics, such monovalent antibody fragments have been shown to have certain advantages over reagents employing intact or whole IgG antibodies including, for example, diminished interference with samples containing rheumatoid factor and/or anti-species IgG antibodies. Independent of the ultimate use, preservation of the molecular integrity of antibodies and their binding activity during reagent synthesis and purification is crucial because the degradation thereof can result in altered antibody performance, and immunoassay performance would suffer as well. Where such intact or whole IgG antibodies are employed as an in vivo immunotherapeutic, serum sickness could occur.

The proteolytic digestion of whole or intact IgG antibodies to obtain F(ab')$_2$ antibody fragments therefrom is well known according to methods known in the art. The proteolytic enzyme pepsin is commonly used for this purpose. For example, F(ab')$_2$ antibody fragments can be prepared by pepsin digestion of whole mouse IgG antibodies [Lamoyi, et al, *J. Immunol. Methods*, Vol. 56, p. 235 (1983)] or rat IgG antibodies [Rousseaux, et al., *J. Immunol. Methods*, Vol. 64, p. 141 (1983)]. However, some antibodies, particularly monoclonal antibodies, are extremely sensitive to pepsin digestion and, in such cases, are rapidly degraded to antibody fragments having reduced or no binding activity. In order to avoid such degradation IgG molecules can instead be digested with preactivated papain [Parham, et al., *J. Immunol. Methods*, Vol. 53, p. 133, (1982)] to yield F(ab')$_2$ and F$_c$ fragments.

Although papain can be employed to digest pepsin-sensitive antibodies as described above, it has nevertheless been observed that even papain digestion can result in a significant increase in the degradation of the molecular integrity of antibody fragments derived therefrom. For example, such degradation results in a decreased number of available sulfhydryl groups in the hinge region and, in some instances, no sulfhydryl groups. Therefore, in such instances where it is desirable to digest whole IgG molecules with papain as described above, the prior art methods do not enable the preparation of intact active F(ab')$_2$ antibody fragments from those whole IgG antibodies which are otherwise susceptible to degradation and inactivation by papain digestion.

Accordingly, it is an object of the present invention to provide a papain-free F(ab')$_2$ antibody fragment preparation derived from papain digested whole IgG antibody.

Another object of the present invention is to provide an F(ab')$_2$ antibody fragment preparation from which Fab' antibody fragments can be obtained having available free sulfhydryl groups in the hinge region.

SUMMARY OF THE INVENTION

In an attempt to determine the source of the observed increase in the degradation of antibody fragments derived from papain-digested whole IgG antibody, the molecular integrity of such fragments, in the presence and absence of a reducing agent and purified by gel filtration, was assessed by SDS-PAGE (sodium dodecylbenzenesulfonate-polyacrylamide gel electrophoresis). Under non-reducing conditions, the F(ab')$_2$ preparations appeared to be substantially pure and structurally intact. However, in the presence of a reducing agent, which should yield both a heavy fragment and a light chain, preparations were degraded to small fragments ($<25,000$ daltons). However, iodoacetamide treatment of the F(ab')$_2$ preparations prior to SDS-PAGE analysis under reducing conditions prevented this degradation from occurring. Accordingly, since it is known that papain is active under reducing conditions in the presence of SDS and that its activity can be completely inhibited by iodoacetamide (Parham, et al., supra), such data suggest papain contamination of the F(ab')$_2$ preparations.

It has also been found that when a mixture comprising intact IgG antibody and a papain-derived F(ab')$_2$ antibody fragment preparation purified by gel filtration was analyzed by SDS-PAGE under reducing conditions, no proteolytic digestion was evident in the presence of iodoacetamide, whereas a high degree of degradation of the sample was observed in the absence of iodoacetamide. Accordingly, such data further support the hypothesis of contamination of the F(ab')$_2$ preparations by papain, a cysteine protease that is activated by reduction, inactivated by alkylation and retains activity in the presence of SDS.

In view of the foregoing, it is therefore believed that the contaminating papain is due to the presence of trace quantities of papain integrated into the antibody fragments. Such integration is most likely the result of a disulfide exchange between the sulfhydryl groups in papain and F(ab')$_2$ molecules during the proteolytic digestion of the whole IgG antibody with papain and/or subsequent purification of the digestion products through covalent attachment to provide, for example, one or more of Fab'-S-S-papain, Fc-S-S-papain, and the like papain-associated digestion products.

Such incorporation of papain into Fab' antibody fragments by disulfide exchange can have detrimental effects on the molecular integrity and binding activity of such antibody fragments following reduction, and are not removable according to methods known in the art such as by gel filtration or ion exchange chromatography. In particular, the suspected papain-associated digestion products were copurified with F(ab')$_2$ by gel filtration and affinity chromatography in the absence of a reducing agent, and cation exchange chromatography was employed in an attempt to separate papain-associated digestion products from F(ab')$_2$. Although it was possible to demonstrate that papain (pI 9.6) is retained by the cation exchange material, the separation of the papain-Fab' conjugate from F(ab')$_2$ was not successful. Alternatively, when purified as described above in the presence of a reducing agent, a papain-free Fab preparation was obtained. However, since it is known that papain digestion in the presence of reducing agents may result in Fab antibody fragments, i.e., having no free sulfhydryl groups, such antibody fragments would therefore be undesirable for immunoassay reagent synthesis purposes according to methods known in the art which require free sulfhydryl groups in the hinge region for labeling an antibody fragment with, for example, an enzyme.

The solution afforded by the present invention is a method for obtaining papain-free antibody fragments derived from papain digested whole IgG antibody employing an antibody to papain for binding to and removing papain-associated digestion products from the preparation. In particular, whole IgG antibody is first treated with papain, preferably activated with a reducing agent, to produce a digested antibody preparation thereof comprising $F(ab')_2$ antibody fragments, Fc (heavy chain) antibody fragments, bulk papain, and any papain-associated digestion products. Bulk papain is removed from the digested antibody preparation and the preparation is treated with an antibody to papain which is added to the mixture for binding to the papain component of any papain-associated digestion products. The $F(ab')_2$ antibody fragments are then separated from the Fc antibody fragments and the antibody-bound papain-associated digestion products, preferably with an immobilized form of a specific binding substance for the antibody to papain and the Fc antibody fragments, to result in an $F(ab')_2$ antibody fragment preparation which is free of papain-associated digestion product contamination.

Accordingly, the method of the present invention is particularly useful for obtaining a papain-free $F(ab')_2$ antibody fragment preparation derived from papain-digested whole IgG antibodies which are otherwise sensitive to pepsin digestion as described above. In particular, the use of an antibody to papain according to the present invention removes any of the papain-associated digestion products from an $F(ab')_2$ antibody fragment preparation which, if present, would result in the degradation of the molecular integrity of Fab' antibody fragments derived therefrom. Furthermore, the presence of such papain-associated digestion products under strong reducing conditions or reducing conditions in the presence of a denaturant such as sodium dodecylbenzenesulfonate could also result in a decrease in the binding activity of the antibody fragments so obtained. Still further, the Fab' antibody fragments obtained from the anti-papain treated $F(ab')_2$ antibody preparation according to the present invention possess free sulfhydryl groups in the hinge region and are therefore highly desirable for use in immunoassay reagent synthesis, as will be described in greater detail hereinafter. Such papain-free $F(ab')_2$ antibody fragment preparations also exhibit superior long-term stability of the $F(ab')_2$ antibody fragments contained therein.

DESCRIPTION OF THE PREFERRED EMBODIMENTS

The immunoglobulin source for whole IgG antibodies for use according to the present invention can be obtained in any available manner, such as conventional antiserum and monoclonal techniques. For example, antiserum can be obtained by well-established techniques involving immunization of an animal, such as a mouse, rabbit, guinea pig or goat, with an appropriate immunogen. The immunoglobulins can also be obtained by somatic cell hybridization techniques, such resulting in what are commonly referred to as monoclonal antibodies, also involving the use of an appropriate immunogen.

Typically, when whole IgG antibodies are digested with papiin in the presence of a reducing agent, the products of digestion, i.e., $F(ab')_2$ antibody fragments, are also reduced to Fab' (sulfhydryl groups) and/or Fab (no sulfhydryl groups) antibody fragments. It is to be understood that whether or not some or all of the reduced digestion products contain Fab antibody fragments will depend upon the particular type of whole IgG antibody which has been digested. However, in either case, the presence of Fab antibody fragments is undesirable where the presence of sulfhydryl groups is necessary to couple, for example, enzymes and the like labels thereto.

In order to obtain Fab' antibody fragments having the necessary sulfhydryl groups required for such coupling techniques, papain can instead be preactivated with a reducing agent followed by gel filtration to separate the preactivated papain from excess reducing agent [Parham, et al., supra]. Accordingly, such procedure results in intact $F(ab')_2$ and Fc antibody fragments which can then be separated according to methods known in the art, such as with a protein A specific binding affinity column. Although any of the bulk papain will be removed according to the methods described above, any papain which is present in the form of Fab'-S-S-papain, Fc-S-S-papain, and the like papain-associated digestion products, will nevertheless be reactivated by the reducing agent employed to reduce the $F(ab')_2$ antibody fragments into the Fab' and Fc antibody fragments thereof. Accordingly, the presence of such papain-associated digestion products under such reducing conditions results in further degradation of the desired Fab' antibody fragments, and could also result in the consequent loss of activity thereof, by such reactivated papain.

According to the present invention, the presence of such papain-associated digestion products, and the aforementioned consequences of the presence thereof, are overcome by employing an antibody to papain which binds to any papain-associated digestion products and enables the removal thereof prior to reduction of the $F(ab')_2$ antibody fragments to Fab' antibody fragments. The antibody to papain can be obtained according to well-established techniques involving the immunization of an animal with papain, and also is commercially available.

In particular, according to the method of the present invention, papain is preferably activated with a reducing agent, such as cysteine, β-mercaptoethanol, dithiothreitol, mercaptoethylamine, and the like reducing agents, preferably cysteine, and then purified by gel filtration, or other methods known in the art, such as ion exchange chromatography, affinity chromatography, dialysis, and the like, to separate the activated papain from excess reducing agent [Parham, et al., *J. Immunol. Methods*, Vol. 53, p. 133 (1982)]. The desired whole IgG antibody is digested with the activated papain, to result in a digested antibody preparation as described above. It is to be understood that according to the present invention, bulk papain can be removed from the digested antibody preparation prior to the treatment thereof with the antibody to papain, or the digested antibody preparation can be treated with the antibody to papain in the presence of the bulk papain. In the latter situation, the antibody to papain is added to the digested antibody preparation in an amount sufficient to bind to all of the bulk papain and any papain-associated digestion products. Accordingly, the antibody binds to bulk papain and any papain associated digested products to form antibody-bound species thereof.

Preferably, bulk papain is removed from the preparation employing, for example, a gel filtration column or other methods known in the art, such as ion exchange chromatography, affinity chromatography, and the like. The purified digested antibody preparation is then treated with the antibody to papain whereby the antibody binds to the papain component of the papain-associated digestion products to form antibody-bound species thereof. In either case, the desired F(ab')$_2$ antibody fragments are then separated from the Fc antibody fragments and the contaminating antibody-bound species to result in a papain-free F(ab')$_2$ antibody fragment preparation. In particular, the Fc antibody fragments and the contaminating antibody-bound species can be removed from the digested antibody preparation according to methods known in the art. For example, an immobilized binding substance which is capable of binding to the Fc antibody fragments and the antibody-bound species can be employed for such purpose. Alternatively, ion exchange chromatography can be employed for such purpose. Preferably, the Fc antibody fragments and the antibody-bound species are separated employing an immobilized form of protein A which is capable of binding to the Fc antibody fragments and the Fc portion of the antibody to papain of the antibody-bound species. For example, the antibody-treated mixture can be eluted through a binding affinity column containing an immobilized form of protein A prepared according to methods known in the art whereby the Fc fragments and the antibody-bound species bind to and are thereby immobilized by the protein A, and the F(ab')$_2$ antibody fragments collected therefrom.

The F(ab')$_2$ antibody fragments obtained according to the present invention are particularly useful for coupling various labels thereto, such as enzymes, fluorescent, phosphorescent, chemiluminescent, bioluminescent and the like molecules; gold and silver sols; latex particles, and the like labels, according to methods known in the art for use as labeled reagents in immunoassays. Preferably, the F(ab')$_2$ antibody fragments are reduced with, for example, cysteine, dithiothreitol, $\beta$-mercaptoethanol, mercaptoethylamine, and the like reducing agents, preferably mercaptoethylamine, according to methods known in the art, to obtain Fab' antibody fragments having maximum binding activity and free sulfhydryl groups in the hinge region for such use.

In particular, such F(ab')$_2$ or Fab' antibody fragments can be treated with a crosslinking reagent such as o-phenylenedimaleimide, bis(maleimido)methyl ester, and the like crosslinking reagents to obtain Fab'- or F(ab')$_2$-maleimido-activated antibody fragments. The maleimido-activated antibody fragments can then be reacted with a selected enzyme to produce a desired enzyme-labeled Fab' or F(ab')$_2$ conjugate thereof according to methods known in the art. Alternatively, where the desired enzyme component is $\beta$-D-galactosidase and the desired antibody component is Fab', coupling can be achieved by first blocking the surface-exposed sulfhydryl groups of $\beta$-D-galactosidase with an alkylating reagent, such as iodoacetamide, and then reacting the alkylated $\beta$-D-galactosidase with a crosslinking reagent, such as succinimidyl-4-(N-maleimidomethyl)-cyclohexane-1-carboxylate [SMCC], to incorporate reactive maleimide groups into the enzyme. Accordingly, when the maleimide-activated $\beta$-D-galactosidase is reacted with the Fab' antibody fragment, the sulfhydryl groups of the Fab' fragment react with the $\beta$-D-galactosidase-maleimide groups to form a covalent bond therebetween to result in a conjugate reaction mixture comprising enzyme-antibody conjugates and unreacted enzyme and antibody components. The conjugate reaction mixture can then be purified according to methods known in the art, preferably according to the method described in commonly assigned U.S. patent application Ser. No. 939,640, filed Dec. 9, 1986, whereby the conjugate reaction mixture is purified by polyacrylamide gel electrophoresis.

Such labeled reagents can be employed in immunoassays for determining the amount of analyte present in a liquid test sample. Generally, such immunoassays involve specific binding interactions between the analyte and a labeled reagent which form a specific binding reaction system comprising two species or forms of the labeled reagent, a bound species and a free species. The relative amount or proportion of the labeled reagent that results in the bound species compared to the free species is a function of the presence or amount of the analyte to be detected in the test sample.

In particular, the present invention will now be illustrated, but is not intended to be limited, by the following examples:

EXAMPLE 1

Preparation of Anti-Thyroxine Monovalent Antibody Fragment (Fab') from Anti-Thyroxine Divalent Antibody Fragment (F[ab']$_2$)

The monovalent antibody fragmnt (Fab') of an anti-thyroxine monoclonal IgG antibody was prepared by preactivated papain digestion of the whole antibody to obtain the divalent antibody fragment (F[ab']$_2$) thereof which was reduced with mercaptoethylamine to obtain the desired monovalent antibody fragment (Fab') as follows:

(a) Preparation of Divalent Antibody Fragment (F[ab']$_2$).

F(ab')$_2$ was prepared from anti-thyroxine IgG monoclonal antibody isolated from ascites fluid (Meloy Laboratories, Inc., Springfield, Va., USA, monoclonal antibody to T$_4$, 156/7) on a Bio-Rad MAPS® protein A column (Bio-Rad Laboratories, Richmond, Calif., USA) to obtain 14.5 mg IgG/mL ascites fluid. Papain [Sigma Chemical Co., St. Louis, Mo., USA, Type III, 2x crystallized from papaya latex in 0.05M sodium acetate suspension, pH 4.5, preactivated by incubating with cysteine followed by gel filtration to obtain active enzyme according to the method described by Parham, et al., *J. Immunol. Methods*, Vol. 53, p. 133 (1982)] was added to the purified IgG (5.8 mL, 1.09 mg/mL) in 0.1M sodium acetate, 3.0 mM EDTA (ethylenediamine tetraacetic acid), pH 5.5 at 0.62 mg/mL (1.02 mL) in a 1:10 weight ratio of papain to IgG. The digsst was incubated for 40 minutes at 37° C., and the products were chromatographed on a 1.0×80.0 cm gel filtration column (AcA44 Ultrogel, LKB, Sweden) in PBS (phosphate buffered saline)/NaN$_3$ buffer to obtain a first peak containing the desired F(ab')$_2$ and Fc antibody fragments and contaminating papain-associated digestion products, and a second peak containing bulk papain.

(b) Removal of Papain-Associated Digestion Products.

The first fraction from step (a) of the present example was treated with polyclonal anti-papain IgG (Cappel, Division of Cooper Diagnostics, Cochranville, Pa., USA, Lot No. 23655, Cat. No. 0100-1202) in order to complex and subsequently isolate the papain contamination from the desired antibody fragment, F(ab')$_2$. To the first gel filtration fraction (4.0 mL, 2.52 mg/mL), 2.0 mg of anti-papain IgG in PBS (1.08 mL, 1.85 mg/mL) was added and incubated overnight at 4° C. The solution was then chromatographed on a Bio-Rad MAPS® protein A column which retained both the original Fc fragment from the digest and the anti-papain IgG which was complexed with the papain-associated digestion products. The purified F(ab')$_2$ passed through the column in the application buffer. Analytical SDS-polyacrylamide gel electrophoresis indicated that the F(ab')$_2$ purified in this way was free of the papain contamination and of high purity. The concentration of F(ab')$_2$ was determined to be 0.44 mg/mL (8.6 mL, 3.77 mg) from the absorbance at 280 nm using an extinction coefficient of 1.48 (cm·mg/mL)$^{-1}$ and a molecular weight of 92,000. The F(ab')$_2$ was stored at 4° C. in PBS/NaN$_3$ buffer.

(c) Reduction of F(ab')$_2$ to Fab'.

The F(ab')$_2$ solution (8.2 mL, 0.44 mg/mL) prepared according to step (b) of the present example was exchanged into 0.1M sodium phosphate, 5.0 mM EDTA buffer (pH 6.0) to a concentration of 0.67 mg/mL (5.1 mL). Mercaptoethylamine was then added to a concentration of 10 mM and incubated for 60 minutes at 37° C. The reducing agent was removed by dialysis against PBS with 5.0 mM EDTA in a stirred ultrafiltration cell (Amicon Corp., Danvers, Mass., USA). The concentration of Fab' (0.63 mg/mL 5.3 mL) was determined from the absorbance at 280 nm using an extinction coefficient of 1.48 (cm·mg/mL)$^{-1}$ and a molecular weight of 46,000 daltons. The sulfhydryl group content of the Fab' was measured with 4,4'-dithiopyridine [Grassetti, et al., *Arch. Biochem. Biophys.*, Vol. 119, p. 41 (1967)] and was determined to be 3 sulfhydryl groups per Fab'.

EXAMPLE 2

Preparation of Activated β-D-Galactosidase

*E. coli* β-D-galactosidase was stored as an (NH$_4$)$_2$SO$_4$ suspension with 0.02% NaN$_3$ at a concentration of 14 mg/mL. The β-D-galactosidase suspension (1.8 mL) was centrifuged to obtain a pellet which was dissolved in PBS to a volume of 2.1 mL (100% enzyme activity) having a concentration of 11.8 mg/mL, 25 mg or 54 nmol (determined from the absorbance at 280 nm using an extinction coefficient of 2.43 (cm·mg/mL)$^{-1}$ and a molecular weight of 465,000). Any sulfhydryl groups on the β-D-galactosidase (typically less than or equal to 3 sulfhydryls) were alkylated in a reaction with a 20-fold molar excess of iodoacetamide for 30 minutes at room temperature in the dark. The reaction mixture was chromatographed on a 1.0×40.0 cm desalting column (BioGel® P-6DG, Bio-Rad Laboratories, Richmond, Calif., USA) in PBS buffer. The β-D-galactosidase peak was concentrated in a stirred ultrafiltration cell (AMICON) to 3.1 mg/mL (7.2 mL, 22 mg, 105% enzyme activity) and a 20-fold molar excess of succinimidyl-4-(N-maleimido-methyl)cyclohexane-1-carboxylate (SMCC, Pierce Chemical Co., Rockford, Ill., USA) was added and the reaction carried out for 1.0 hour at room temperature with gentle stirring. The SMCC reaction mixture was desalted on a 1.0×40.0 cm desalting column (BioGel® P-6DG) in PBS containing 1.0 mM EDTA in a volume of 7.2 mL at 3.0 mg/mL (92% enzyme activity). The maleimide content of the activated β-D-galactosidase which eluted from the column was calculated from the difference between the sulfhydryl group content (determined with 4,4'-dithiopyridine) of reduced glutathione in the absence and the presence of activated β-D-galactosidase, which was determined to be 5.4 maleimides/mole of β-D-galactosidase.

EXAMPLE 3

Preparation of Anti-Thyroxine-β-D-Galactosidase Conjugate

Activated β-D-galactosidase (23.6 nmoles) in 3.5 mL PBS (prepared as in Example 2) was combined with 59.0 nmoles of anti-thyroxine Fab' (prepared as in Example 1) in 4.3 mL PBS, 5 mM EDTA. The reaction solution was incubated for 20 hours at 5° C. The resulting Fab'-β-D-galactosidase conjugate preparation was exchanged into PBS/NaN$_3$ buffer and stored at 4° C.

What is claimed is:

1. A method for preparing a papain-free F(ab')$_2$ antibody fragment preparation derived from papain digested whole IgG antibody, said method comprising the steps of:
   (a) digesting said whole IgG antibody with papain to produce a digested antibody preparation thereof comprising F(ab')$_2$ antibody fragments, Fc antibody fragments, papain associated digestion products, and bulk papain;
   (b) removing said bulk papain from and treating said digested antibody preparation with an antibody to papain whereby said antibody binds to said papain associated digestion products to form antibody-bound species thereof; and
   (c) separating said F(ab')$_2$ antibody fragments from said Fc antibody fragments and said antibody-bound species.

2. The method of claim 1 wherein said bulk papain is removed by binding to said antibody to papain to form antibody-bound species thereof.

3. The method of claim 1 wherein said bulk papain is removed prior to treating said digested antibody preparation with said antibody to papain.

4. The method of claim 3 wherein said bulk papain is removed by gel filtration.

5. The method of claim 1 wherein said papain is activated with a reducing agent selected from the group consisting of cysteine, β-mercaptoethanol, dithiothreitol and mercaptoethylamine.

6. The method of claim 1 further comprising the step of reducing said F(ab')$_2$ antibody fragments to Fab' antibody fragments thereof.

7. The method of claim 6 wherein said reducing agent is selected from the group consisting of cysteine, dithiothreitol, β-mercaptoethanol, and mercaptoethylamine.

8. The method of claim 1 wherein said antibody-bound species and said Fc antibody fragment of step (b) are separated with an immobilized form of a specific binding substance for said papain antibody and said Fc antibody fragment whereby said antibody-bound species and said Fc fragment are immobilized thereto.

9. The method of claim 8 wherein said immobilized form of said specific binding substance for said antibody to papain and said Fc antibody fragment is protein A.

10. The method of claim 1 wherein said whole IgG antibody is a monoclonal IgG antibody.

11. A papain-free F(ab')$_2$ divalent antibody fragment preparation prepared according to the method of claim 1.

* * * * *